(12) United States Patent
McWhorter et al.

(10) Patent No.: US 9,656,865 B2
(45) Date of Patent: May 23, 2017

(54) USE OF STORAGE-STABLE AQUEOUS SOLUTIONS OF CHLORINE DIOXIDE TO GENERATE PURE CHLORINE DIOXIDE GAS FOR DECONTAMINATION

(75) Inventors: Thomas Ellsworth McWhorter, Allentown, PA (US); Aaron Rosenblatt, New York, NY (US); Madhu Anand, Allentown, PA (US); John Peter Hobbs, Lansdale, PA (US)

(73) Assignee: CDG ENVIRONMENTAL, LLC, Allentown, PA (US)

( * ) Notice: Subject to any disclaimer, the term of this patent is extended or adjusted under 35 U.S.C. 154(b) by 1784 days.

(21) Appl. No.: 12/296,051

(22) PCT Filed: Apr. 5, 2007

(86) PCT No.: PCT/US2007/066081
§ 371 (c)(1),
(2), (4) Date: Nov. 11, 2008

(87) PCT Pub. No.: WO2007/118159
PCT Pub. Date: Oct. 18, 2007

(65) Prior Publication Data
US 2009/0142226 A1    Jun. 4, 2009

Related U.S. Application Data

(60) Provisional application No. 60/744,374, filed on Apr. 6, 2006.

(51) Int. Cl.
*A61L 2/20* (2006.01)
*C01B 11/02* (2006.01)
*A61L 2/22* (2006.01)

(52) U.S. Cl.
CPC .............. *C01B 11/022* (2013.01); *A61L 2/20* (2013.01); *A61L 2/22* (2013.01)

(58) Field of Classification Search
CPC ............. C01B 11/022; A61L 2/20; A61L 2/22
(Continued)

(56) References Cited

U.S. PATENT DOCUMENTS 2,309,457 A    1/1943   Hutchinson
4,430,226 A    2/1984   Hegde
(Continued)

FOREIGN PATENT DOCUMENTS

WO    9924356    5/1999

OTHER PUBLICATIONS

Rosenblatt, David et al. "The REaction of Chlorine Dioxide with Triethlylamine in Aqueous Solution." J. Org. Chem. (1963) 28 (10) 2790-2794.*
(Continued)

*Primary Examiner* — Timothy Cleveland
(74) *Attorney, Agent, or Firm* — Ratnerprestia

(57) ABSTRACT

New methods are disclosed for decontaminating surfaces and enclosures that avoid problems such as salt deposits, corrosion and condensation that accompany the use of known methods. The methods involve the use of chlorine dioxide solutions prepared by passing dilute chlorine gas over solid granular sodium chlorite to produce chlorine dioxide gas which is then collected to form a solution with very low levels of impurities. The chlorine dioxide gas can be introduced into an enclosure and used to disinfect a portion of the contents of the enclosure.

22 Claims, 4 Drawing Sheets

(58) Field of Classification Search
USPC .................................. 422/27–30, 33, 37, 305
See application file for complete search history.

(56) References Cited

U.S. PATENT DOCUMENTS

| | | | |
|---|---|---|---|
| 4,681,739 A | 7/1987 | Rosenblatt et al. | |
| 4,853,270 A | 8/1989 | Wycech | |
| 4,948,641 A | 8/1990 | Shantz | |
| 5,006,326 A | 4/1991 | Mayurnik et al. | |
| 5,039,423 A | 8/1991 | Kelley | |
| 5,110,580 A | 5/1992 | Rosenblatt et al. | |
| 5,182,122 A | 1/1993 | Uehara | |
| 5,234,678 A | 8/1993 | Rosenblatt | |
| 5,770,135 A | 6/1998 | Hobbs | |
| 5,855,861 A | 1/1999 | Lee | |
| 6,051,135 A | 4/2000 | Lee | |
| 6,284,152 B1 | 9/2001 | Kross | |
| 2002/0037248 A1 | 3/2002 | Bechberger | |
| 2003/0215381 A1 | 11/2003 | Rosenblatt | |
| 2004/0022667 A1* | 2/2004 | Lee et al. .......................... | 422/4 |
| 2004/0211746 A1 | 10/2004 | Trude | |
| 2005/0079230 A1 | 4/2005 | Lee | |
| 2007/0098591 A1* | 5/2007 | Frinke et al. ................... | 422/33 |
| 2011/0233147 A1 | 9/2011 | Hayafuji | |

OTHER PUBLICATIONS

Young, J. F. "Humidity Control in the Laboratory Using Salt Solutions—A Review." J. appl. Chem (1967) 17 241-245.*
Australian Office Action for Australian Patent Application No. 2006332600 mailed Dec. 20, 2010.
Australian Office Action for Australian Patent Application No. 2006332600 mailed May 6, 2011.
Canadian Office Action for CA 2,629,888, dated Oct. 17, 2012.
Canadian Office Action for CA 2,675,574 dated Feb. 7, 2013.
Desai, U.J., "Comparative Analytical Methods for the Measurement of Chlorine Dioxide," Masters Thesis—Environmental Engineering, Virginia Polytechnic Institute and State University, Blacksburg, VA, 2002.
Entire patent prosecution history of U.S. Appl. No. 12/296,049, filed Apr. 21, 2010, entitled, "Storage-Stable Aqueous Solutions of Chlorine Dioxide and Methods for Preparing and Using Them."
Entire patent prosecution history of U.S. Appl. No. 13/365,869, filed Feb. 3, 2012, entitled, "Storage-Stable Aqueous Solutions of Chlorine Dioxide and Methods for Preparing and Using Them."
Entire patent prosecution history of U.S. Appl. No. 13/365,885, filed Feb. 3, 2012, entitled, "Storage-Stable Aqueous Solutions of Chlorine Dioxide and Methods for Preparing and Using Them."
Entire patent prosecution history of U.S. Appl. No. 13/365,902, filed Feb. 3, 2012, entitled, "Storage-Stable Aqueous Solutions of Chlorine Dioxide and Methods for Preparing and Using Them."
Entire patent prosecution history of U.S. Appl. No. 13/365,912, filed Feb. 3, 2012, entitled, "Storage-Stable Aqueous Solutions of Chlorine Dioxide and Methods for Preparing and Using Them."
EPA Guidance Manual on Alternative Disinfectants and Oxidant: Chlorine Dioxide, Apr. 1999, p. 4-1:4-41.
Finch, G.R., et al., "Synergistic Effects of Multiple Disinfectants," AWWA Research Foundation and American Water Works Association, 2000.
European Search Report EP 06 84 9144, Issued Aug. 6, 2013.
Harris, C.L., "The Effect of Predisinfection with Chlorine Dioxide on the Formation of Haloacetic Acids and Thihalomethanes in a Drinking Water Supply," Masters Thesis—Environmental Engineering, Virginia Polytechnic Institute and State University, Blacksburg, VA, 2001.
International Search Report dated Dec. 6, 2007 for International Application No. PCT/US2006/060879.
International Search Report dated Jul. 3, 2008 for International Application No. PCT/US2007/066081.
Li, H. et al., "Sequential Disinfection Design Criteria for Inactivation of Cryptosporidium Oocysts in Drinking Water," AWWA Research Foundation and American Water Works Association, 2001.
Lindner, Nora, International Preliminary Report on Patentability dated May 14, 2008 for International Application No. PCT/US2006/060879.
Noss, C.L. and V.P. Olivieri, "Disinfecting capabilities of oxychlorine compounds," Appl. Environ. Microbiol. 1985,vol. 50, No. 50, pp. 1162-1164.
Singh, N., et al., "Efficacy of chlorine dioxide, ozone, and thyme essential oil or a sequential washing in killing *Escherichia coli* O157:H7 on lettuce and baby carrots," Lebensm.-Wiss u.-Technol., 35, (2002) 720-729.
Canadian Search Report CA 2,629,888, Issued October 7, 2013.
Water Boy 2011, Retrieved online at http://www.waterboyinc.com/blog/distilled-and-purified-water/.
White, G.C., "Handbook of Chlorination and Alternative Disinfectants," Wiley Interscience, 1999.
Written Opinion of the International Searching Authority mailed Jul. 3, 2008 for International Application No. PCT/US2007/066081.
Notice of Allowance for U.S. Appl. No. 13/365,885, Issued Dec. 31, 2014.
Notice of Allowance for U.S. Appl. No. 13/365,902 Issued Dec. 24, 2014.
Notice of Allowance for U.S. Appl. No. 13/365,869 Issued Dec. 10, 2014.
Office Action, dated Dec. 16, 2013, corresponding to counterpart Canadian Patent Application No. 2675574.
Bohner et al., Corrosivity of chlorine dioxide used as sanitizer in ultrafiltration systems, *Journal of Dairy Science*, 74 (10), 3348-3352, Oct. 1991.
Canadian Office Action for CA 2,629,888, Dated Sep. 11, 2014.
U.S. Office Action for U.S. Appl. No. 12/296,049, Dated Sep. 26, 2014.
Canadian Office Action for CA 2,675,574 Dated Oct. 6, 2014.
Chart of References (undated).
Canadian Office Action dated Feb. 26, 2016 for Canadian Application No. 2,629,888.
Canadian Examination Report dated Mar. 16, 2016 for Canadian Application No. 2,675,574.
Halox Technologies, Inc., Material Safety Data Sheet, Chlorine Dioxide Dissolved in Water, < 0.054% (w/w), Jun. 21, 20014, http://www.haloxtech.com/pd/MSDS-Chlorinedioxide (ClO2)-540ppm.pfd.
Notice of Allowance for U.S. Appl. No. 14/824,548, dated Oct. 13, 2016, 22 pages.
European Examination Report for European Application No. 06849114.8, dated Aug. 19, 2016, 6 pages.
Canadian Office Action for Canadian Application No. 2675574, dated Aug. 12, 2016, 4 pages.

* cited by examiner

USE OF STORAGE-STABLE AQUEOUS SOLUTIONS OF CHLORINE DIOXIDE TO GENERATE PURE CHLORINE DIOXIDE GAS FOR DECONTAMINATION

CROSS REFERENCE TO RELATED APPLICATIONS

The present application is a national stage of International Application No. PCT/JP2007/066081 filed on Apr. 5, 2007 and claims priority to U.S. Provisional Patent Application No. 60/744,374 filed on Apr. 6, 2006, the disclosures of which are incorporated herein by reference.

BACKGROUND

Chlorine dioxide is a strong, but highly selective oxidizer. It can be used in aqueous solution for disinfecting drinking water and in other water processing applications. One of its chief benefits is that it does not react with organic materials to form chlorinated hydrocarbons which have been shown to cause health problems. In fact, chlorine dioxide not only destroys organic compounds but also destroys hazardous chlorinated hydrocarbons, once formed. Solutions of chlorine dioxide can also be used as a disinfectant for the decontamination of bio-contaminated buildings, enclosures, and articles and as a disinfecting wash for poultry, beef, and many types of fruits and vegetables.

Chlorine dioxide can also be used in the gas phase as a disinfectant. The gas can be used to sterilize medical instruments and other medical articles, as described in U.S. Pat. No. 4,681,739. The gas has been used to decontaminate buildings containing Anthrax spores after the Anthrax attacks of 2001. The gas can also be used for decontamination of buildings infested with mold and as a decontaminant for bio-safety cabinets and other laboratory enclosures.

Liquids called "Stabilized Chlorine Dioxide," "Chlorine Dioxide Solution" and the like have been commercially available in the past but these liquids do not contain chlorine dioxide; rather, they contain sodium chlorite. When mixed with acid sodium chlorite reacts to produce chlorine dioxide, but this requires chemical mixing and handling of acid. Opportunities abound for errors in mixing and, even when reagents are mixed properly, the resulting solution contains high levels of salts, acids, and other impurities. Moreover, such chlorine dioxide solutions have a short shelf life once they are mixed.

Chlorine dioxide can be produced in a variety of ways. Most of the production processes that are suitable for less than a few thousand pounds per day are based on reaction of sodium chlorite with chlorine or acid in an aqueous solution. Many of these processes are based on the reaction:

$$2NaClO_2 + Cl_2 => 2ClO_2 + 2NaCl \quad \text{Reaction 1}$$

Which can be carried out in an aqueous solution, or in the absence of water in what is known as the Gas:Solid™ ClO₂ process.

Other production processes involve mixing dissolved sodium chlorite and hydrochloric acid, (Reaction 2), or mixing dissolved sodium chlorite with hydrochloric acid and sodium hypochlorite solution (Reaction 3).

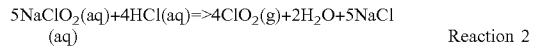
$$5NaClO_2(aq) + 4HCl(aq) => 4ClO_2(g) + 2H_2O + 5NaCl(aq) \quad \text{Reaction 2}$$

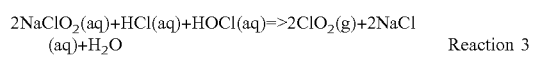
$$2NaClO_2(aq) + HCl(aq) + HOCl(aq) => 2ClO_2(g) + 2NaCl(aq) + H_2O \quad \text{Reaction 3}$$

where (aq) refers to an aqueous solution and (g) refers to both evolved and dissolved gas There are several drawbacks to these production methods. First, the products are impure. In addition to chlorine dioxide, product solutions also contain the other products and by-products of the reaction and unreacted feedstock reagents. Typical contaminants in these products include hydrochloric acid, sodium hypochlorite, sodium chlorite, sodium chlorate, chlorine and sodium chloride. In addition, the reactions are exothermic and produce substantial amounts of heat.

In response to the Anthrax attacks of 2001, several buildings were decontaminated using chlorine dioxide gas produced in solution using Reaction 3. The production of chlorine dioxide gas for the decontamination required pumping product solution of Reaction 3 through packed columns and blowing air over the solution to strip the dissolved chlorine dioxide from the solution into the air. The gas was then blown into the space to carry out decontamination. Despite its complexity, this process was very effective at killing Anthrax spores. Nevertheless, several reported problems with this method reduced its effectiveness.

As chlorine dioxide gas is stripped out of solution in this method, micro-droplets of solution became entrained in the resulting gas stream and were carried into the building. These droplets deposited a corrosive mixture of water and contaminants throughout the building space causing severe corrosion and other damage. Even where there was no corrosion, salt deposits had to be removed after decontamination was complete. In addition, the solution became hot as it was produced and when pumped into the stripper column (material transfer device) and contacted with air heated by the blowers, the gas stream was warm and humid. This resulted in severe condensation within the building when the warm, humid air contacted cooler air and cooler surfaces in the building. Large mechanical cooling units were used to partially dehumidify the air but a method was never found to control humidity and chlorine dioxide gas concentration simultaneously.

Thus, new methods are needed for decontaminating surfaces and enclosures that avoid problems such as salt deposits corrosion and condensation that accompany the use of previously known methods.

SUMMARY

New compositions and methods are disclosed for decontaminating surfaces and enclosures that avoid problems such as salt deposits, corrosion and condensation that accompany the use of known methods. The process involves the use of aqueous chlorine dioxide solutions prepared by passing dilute chlorine gas over solid granular sodium chlorite to produce a chlorine dioxide-containing gas mixture by the GAS:SOLID™ chlorine dioxide system process, which is then collected in solution. Unlike liquid phase production technologies, this process produces a contaminant-free liquid product that does not contain chlorine, sodium chlorite, sodium chlorate, or sodium chloride, since these materials do not exist to any appreciable degree in the gas form. Chlorine dioxide solutions produced in this process can have a purity of over 99.95% where purity is measured as the percent of non-aqueous content that is chlorine dioxide.

A process is disclosed for handling chlorine dioxide that includes producing a chlorine dioxide gas and mixing the gas with a carrier gas to produce a gas stream containing chlorine dioxide and disinfecting an enclosure. The gas can be produced by releasing chlorine dioxide gas from an aqueous chlorine dioxide solution containing less than 10% by weight of any of hydrochloric acid, hypochlorite ion, hypochlorous acid, or sodium chloride or it can be produced directly for use, as described above. When solutions are used it is preferred that they contain no more than 5%, or more preferably 2.5%, 1%, 0.5%, 0.2% or even most preferably 0.05% by weight of the above contaminants and even more preferably of total contaminants.

In a method the carrier gas can be air.

In a method the carrier gas can be released from the aqueous chlorine dioxide solution by bubbling the carrier gas through the aqueous chlorine dioxide solution.

In a method the chlorine dioxide gas can be released from the aqueous chlorine dioxide solution by bubbling the carrier gas through the solution wherein the rate of $ClO_2$ gas production can be controlled by the rate of carrier gas flow into the solution.

In a method the chlorine dioxide gas can be released from the aqueous chlorine dioxide solution under a vacuum.

In a method, the chlorine dioxide gas can be released from solution by contacting the solution with the gas in the enclosure. Any method of contacting can be used, for example the chlorine dioxide solution can be sprayed or pumped or atomized into the enclosure. This method is particularly useful for decontaminating beverage tanks or water pipes where limiting humidity during disinfection is not important. Alternatively, the gas or air in an enclosure can be percolated through the solution.

In a method, the chlorine dioxide gas can be released from solution by using a packed column or other high surface area contactor to contact an air stream with the chlorine dioxide solution and then blowing the air/chlorine dioxide stream into an enclosure.

In a method the chlorine dioxide gas can be released from the aqueous chlorine dioxide solution by heating the aqueous chlorine dioxide solution.

In a method the chlorine dioxide gas can be introduced into an enclosure.

In a method the chlorine dioxide gas is introduced into an enclosure and used to disinfect a portion of the contents of the enclosure.

In a method the concentration of chlorine dioxide gas and the humidity are controlled within the enclosure. To this end the relative humidity can be controlled by raising or lowering the temperature of the aqueous chlorine dioxide solution that contacts the carrier gas stream.

In a method the transfer device used to transfer chlorine dioxide gas into the gas phase can also be used to transfer chlorine dioxide gas out of the air or carrier gas in the enclosure. Optionally, the solution used in the scrubber can contain a reducing compound such as sodium thiosulfate.

The method can be used to disinfect a variety of enclosures including bio-safety cabinets freezers, incubators and lyophilizers, a building or a portion of a building, or a tank or pipe.

Additional features and advantages are described herein, and will be apparent from, the following Detailed Description and the figures.

DETAILED DESCRIPTION

Figure 1:
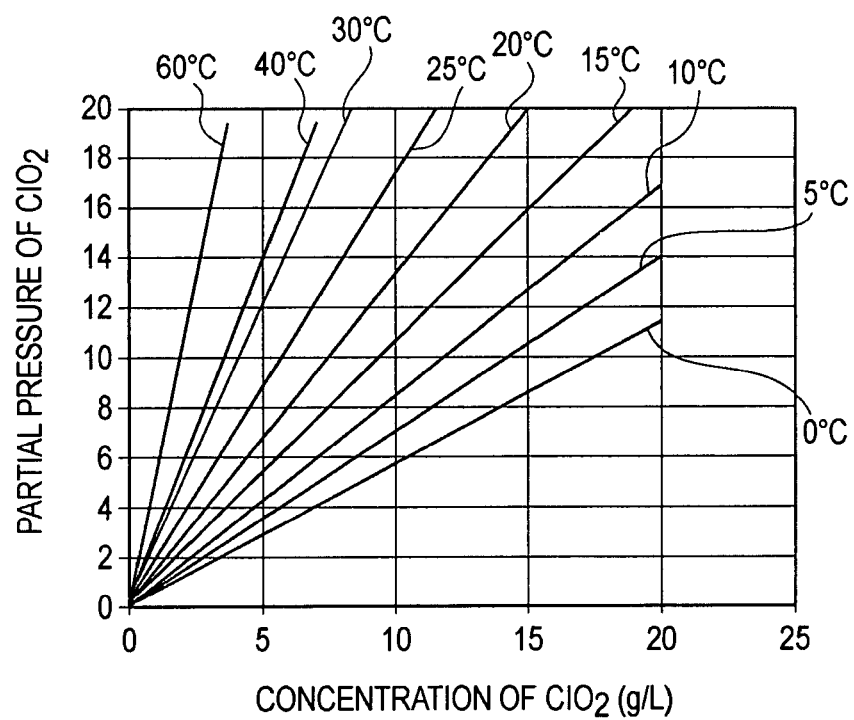
FIG. 1 shows the vapor pressure (expressed in units of kPa) of chlorine dioxide above the surface of aqueous solutions as a function of the solution concentration at different temperatures.

In one aspect a process for handling chlorine dioxide is disclosed. The process involves releasing chlorine dioxide gas from an aqueous chlorine dioxide solution wherein the solution contains less than 10% by weight of either hydrochloric acid, hypochlorite ion, hypochlorous acid, or sodium chloride. More preferably, the solution contains less than 10% by weight of total impurities. The process also involves mixing the released chlorine dioxide gas with a carrier gas to produce a gas stream that contains chlorine dioxide. Once generated, the gas stream can be used as a disinfectant.

One method for making the chlorine dioxide solutions of the invention which contain low amounts of impurities is by passing a dilute chlorine gas over solid granular sodium chlorite to cause a reaction. The reaction proceeds according to Reaction 1 at the interface between the gas and the granules and produces gaseous chlorine dioxide which can then be collected in aqueous solution. This method differs from other production technologies in that the reaction occurs at the interface between the chlorine gas and solid sodium chlorite to produce a gas free of nongaseous reaction products and reactants including sodium chlorite, sodium chlorate, or sodium chloride. The gas can then be conveyed from the location of the reaction and passed through a solution where the chlorine dioxide can be dissolved. The resulting solution can have a chlorine dioxide purity of over 90% by weight on a water free basis. In other words, the non-aqueous content of the solution is more than 90% pure chlorine dioxide. More preferably the solution can have a chlorine dioxide purity of over 95%, still more preferably over 97.5%, 99%, 99.5%, 99.8% or even most preferably 99.95% pure by weight.

Any suitable carrier gas can be used in the invention so long as it does not destabilize either the solution or the chlorine dioxide gas stream produced. For example, the carrier gas can be air, an inert gas or any other gas in which chlorine dioxide is stable throughout the disinfection process. Air in contact and in equilibrium with a solution containing 3 g/L of chlorine dioxide at 20° C. will contain about 4-5% chlorine dioxide by volume. Since the concentration required for gas phase disinfection and decontamination is about 1-2 orders of magnitude lower than this concentration, using air as a carrier gas can remove 90-99%+ of the dissolved chlorine dioxide from a stock solution. In some methods, the solution container can be heated or, alternatively, placed under vacuum to recover a higher percentage of $ClO_2$.

Many suitable methods for releasing the chlorine dioxide gas from solution are known and can be used. For example, the chlorine dioxide gas can be released from the aqueous chlorine dioxide solution by bubbling a stream of a carrier gas through the solution. This method has the advantage that the rate of chlorine dioxide gas production can be controlled by the rate of carrier gas flow through the solution.

This first chlorine dioxide containing stream may be used directly, or further diluted by blending with a second, or multiple, carrier gas stream(s) to produce one or more chlorine dioxide containing streams.

Alternatively, chlorine dioxide gas can be released from the aqueous chlorine dioxide solution under a vacuum, and the released gas mixed into a carrier gas stream. Chlorine dioxide gas can also be released by heating the aqueous chlorine dioxide solution and the released gas can then be passed into a carrier gas stream by standard methods. In addition, the aqueous chlorine dioxide solutions can be produced at the location of use.

Also disclosed are embodiments which can generate chlorine dioxide gas and direct the gas to enclosures ready for disinfection. Also disclosed are embodiments of such disinfection procedures, where a portion of the gas within the enclosure is withdrawn from the enclosure and used as the carrier gas for extracting chlorine dioxide from a solution and returning substantially all of the carrier gas to the enclosure. Enclosures suitable for gas phase decontamination range in size from a few milliliters to full-sized buildings. In general, these systems have a source of chlorine dioxide gas, an analyzer of chlorine dioxide gas concentration, a scrubber to remove the chlorine dioxide from the air following decontamination, a blower to control the flow of air to and from the enclosure and a device to control the humidity in the enclosure.

Where the chlorine dioxide gas is generated at the site of use such a system can contain a source of gaseous chlorine, either as 100% chlorine in liquid form or compressed gas containing chlorine at <5% in nitrogen. For safety reasons chlorine dioxide cannot exceed about 140 mm Hg partial pressure (about 18%) at atmospheric pressure. However, a wide margin of safety is usually provided such that chlorine gas feed for a GAS:SOLID™ chlorine dioxide system is usually no more than about 30 mm Hg (4% at atmospheric pressure which would produce chlorine dioxide at about 7.7%). In systems using pure chlorine, provision can be made for diluting the chlorine with ambient air (or an inert gas), and redundant interlocks can be provided to ensure that the concentration of the feed gas can never exceed safe limits. The chlorine containing gas is preferably passed through cartridges of thermally stable solid sodium chlorite to generate chlorine dioxide gas. These cartridges are commercially available from CDG Research Corporation of Allentown, Pa.

Systems can contain an analyzer for measuring the concentration of chlorine dioxide in the enclosure being disinfected. Such analyzers are available from Optek Danulat of Essen Germany, CDG Research Corporation of Bethlehem, Pa. and other suppliers.

The systems can contain a scrubber or material transfer device to remove or otherwise destroy the chlorine dioxide vented from the enclosure after decontamination is complete. Scrubbers are manufactured by CDG Research Corporation of Bethlehem, Pa., Koch-Glitsch of Wichita, Kans., as well as other suppliers. Many scrubbers operate by contacting the gas to be scrubbed with an aqueous solution of chemicals that react with the contaminant and remove it from the carrier gas. In one embodiment of a packed column scrubber, gas containing chlorine dioxide to be scrubbed can be introduced at the bottom of a column, and scrubber fluid can be introduced at the top. The column can be filled with any suitable gas scrubbing packing that is inert to chlorine dioxide and other gases in the product mix. One suitable material is the plastic FLEXIRING® random packing made by Koch-Glitsch. The scrubber solution for removal of chlorine dioxide can contain one or more dissolved chemical reducing agents such as sodium sulfite, sodium thiosulfate, or sodium metabisulfite, and can contain other chemicals such as sodium hydroxide. In order to minimize the production of liquid byproduct from such a scrubber and obtain the maximum utility of the reducing agents the scrubber solution is usually recovered from the base of the scrubber and recirculated to the top.

One characteristic of both packed column scrubbers and liquid spray scrubbers is that they tend to raise the humidity of the gas being purified. This effect is significant in the typical chlorine dioxide scrubber because the reaction between chlorine dioxide and the dissolved reducing agent is typically exothermic, and the scrubber solution is recirculated. Water from the solution evaporates into the gas being scrubbed as the system heats.

The increase in humidity of the carrier gas in the scrubber is not usually a problem if the gas is vented directly to atmosphere. However, if the gas is recirculated between the scrubber and the enclosure, the warm humid air from the scrubber enters the enclosure where it may cool and form condensation. This condensation may cause severe damage to the enclosure and to articles contained therein. In such a situation it may be necessary or at least advantageous to cool the scrubber.

The systems can contain one or more blowers to draw the air containing chlorine dioxide from the enclosure through the scrubber to destroy the chlorine dioxide so that the air can be rendered safe after the decontamination cycle. In some embodiments, the blower may be used to circulate gas from the enclosure being contaminated to the decontamination system and back. This type of configuration can be used to enhance gas mixing in the enclosure.

The systems can contain a humidifier to raise the humidity in the enclosure to 65-80% relative humidity and a hygrometer to measure the relative humidity in the enclosure. Humidity in this range optimizes the effective kill of some microorganisms such as Anthrax. Humidity in excess of 80% is undesirable because it does not enhance the effectiveness of decontamination and it may lead to "collateral damage" to the enclosure and its contents due to water condensation. Humidity can be added in the form of steam from a steam generator, mist from a nebulizer, or by contacting the enclosure air with water as in a packed tower scrubber. Humidity can be reduced by contacting the gas in or entering the enclosure with a desiccant that is stable and non-destructive to chlorine dioxide, or with a reduced temperature surface such as one might obtain by using a packed bed scrubber with ice or cold water.

The disclosure encompasses a variety of methods for introducing a chlorine dioxide gas stream into an enclosure. The method can work for any disclosure in which a disinfecting amount of chlorine dioxide gas can be introduced and be maintained in the enclosure for a sufficient period of time to allow the gas to disinfect an exposed surface in the enclosure. Suitable enclosures include pipes, storage tanks, tunnels; buildings; houses; cabinets including, bio-safety cabinets, freezers, incubators and lyophilizers; closets; dishwashers; ovens; refrigerators; passenger and storage compartments; interiors of transportation vehicles including airplanes, railcars, ships, shipping containers, boats, automobiles and the like. In addition, enclosure can be used to hold other objects which can also be disinfected by the introduction of chlorine dioxide gas.

In one method, the invention covers decontamination of surfaces using chlorine dioxide gas. Suitable surfaces include any surface that is capable of harboring viruses, spores, bacteria or other infectious microorganisms and that is reasonably stable to contact with chlorine dioxide gas.

Figure 2:
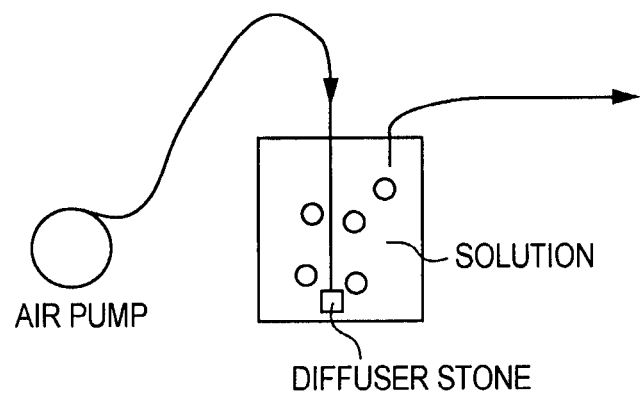
FIG. 2 illustrates a simple decontamination system.
Figure 3:
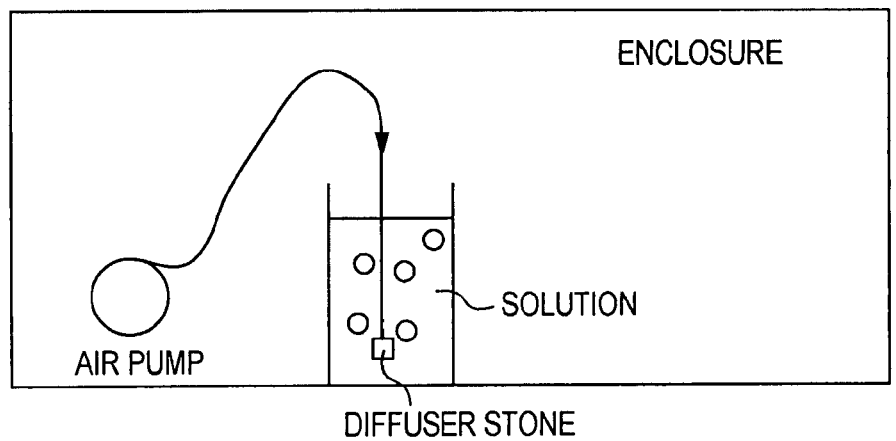
FIG. 3 illustrates Decontamination with Solution inside Enclosure

In one method the aqueous chlorine dioxide solution can be placed in a container and enclosed by a lid. The container can be placed in an enclosure and an opening can be established in the lid. The air in the enclosure will then be exposed to the chlorine dioxide gas released from the container. In this method the rate of release of the chlorine dioxide gas into the air in the enclosure can be controlled by the size of the opening in the lid. One method and corresponding system of the invention is illustrated in FIGS. 2 and 3. In the system illustrated by FIG. 3 an ultra-pure solution of chlorine dioxide is positioned inside an enclosure to be decontaminated and the cap has been removed from the container. In the illustrated method, air from inside the enclosure can be pumped to an air diffusing device, such as a diffuser stone, that is submerged in the solution. In small scale processes, this can be accomplished using a compressor for small scale applications as an aquarium air pump, as sold in many pet stores. Clearly, the process is scaleable and can be scaled up to larger rooms and buildings. The system illustrated in FIG. 3 can be used to release low concentrations of chlorine dioxide over long periods into a food storage container to suppress the growth of mold or other organisms.

Figure 4:
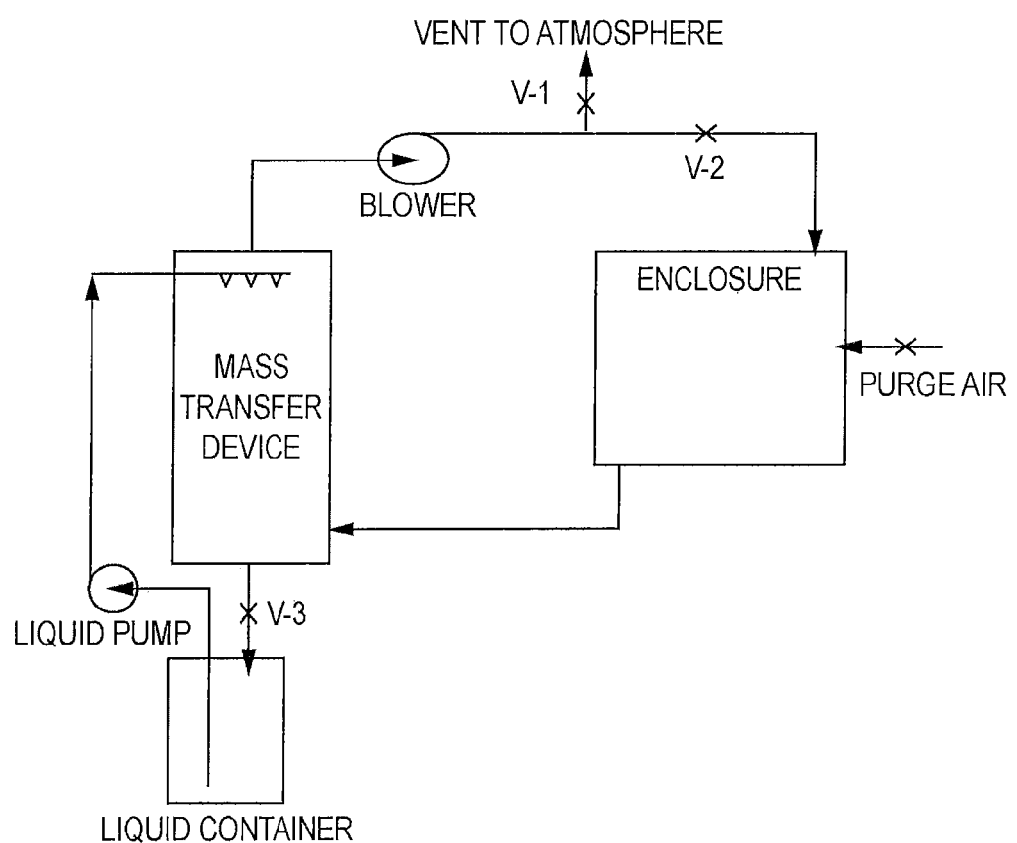
FIG. 4 illustrates A Decontamination System with Multi-purpose Mass Transfer Device

Alternatively, the solution container can be kept outside the enclosure and equipped with at least two ports, as illustrated in FIG. 4. Using such a system, air containing chlorine dioxide can be conducted from the liquid container into the enclosure either directly or through a conduit as shown. In a method, a fan can be provided in the enclosure to accelerate gas distribution. In the illustrated configuration such a system can also be adapted to contain one or more packed scrubber column(s) for transferring the chlorine dioxide into the carrier gas stream.

In a method, the system can be configured with one or more chlorine dioxide removal scrubber(s) to prevent the release of chlorine dioxide into the atmosphere when the gas is cleared from the enclosure. In such systems, when the disinfection is complete the air pump can direct the air through the chlorine dioxide removal scrubbers and either vented to the environment or returned to the enclosure. This scrubbing phase may be continued as long as necessary until the chlorine dioxide is completely eliminated from the enclosure or it is safe to open.

In a method, the system can be configured with one (or more) scrubber(s) wherein the scrubber may first serve to deliver the chlorine dioxide from an aqueous solution to the carrier gas and/or to control the humidity within the enclosure, by recirculating the carrier gas between the enclosure and the system. And then subsequent to the disinfection of the enclosure chlorine dioxide removal chemicals are added to the scrubber solution and the same scrubber may be used to remove the chlorine dioxide from the carrier gas extracted from the enclosure, where the chlorine dioxide depleted carrier gas may be either returned to the enclosure or discharged to the environment.

Generally a complete decontamination treatment cycle includes a humidification phase, a gas fill, a holding phase, and a vent/scrub phase. Sometimes these phases overlap. For example, some practitioners believe that it is advantageous to fill the enclosure with chlorine dioxide gas at the same time that humidity is being added, while others believe that it is advantageous to pre-humidify the enclosure and allow the enclosure and its contents to equilibrate with the higher humidity for a time before adding chlorine dioxide.

A typical decontamination cycle can be carried out by first establishing a suitable level of humidity in the chamber. Generally, it is preferred to establish a relative humidity in the enclosure in the range of about 65% to about 80% before introducing the chlorine dioxide, although wider ranges can also work. Lower humidity reduces the efficacy of killing certain microorganisms. Higher humidity can cause unwanted condensation and corrosion in the enclosure. Since enclosures can be located in air conditioned or otherwise low-humidity areas, it can be necessary to increase the humidity to the desired operating range. Moreover, during this initial humidification phase of the cycle, it is preferred to add humidity to the enclosure as rapidly as possible to minimize the cycle time. To accomplish this, gas can be passed from the enclosure through the packing material of the material transfer device, illustrated in FIG. 4, while circulating water through the packing. The rate of humidification can be increased dramatically by heating the water that recirculates through this device. In situations where the ambient humidity is higher than 80%, the humidity in the enclosure can be lowered by cooling the water recirculating in the mass transfer device.

In this embodiment, the temperature of the circulating liquid in the material transfer device can be controlled by using electrical resistance heaters (e.g. heat tape) to increase temperature, and refrigerators for cooling, such as small thermoelectric or freon refrigerators. For smaller, simpler systems it is adequate to supply hot or cool solutions at the beginning of the cycle. In one suitable method humidifier water can be supplied at about 140° F. and chlorine dioxide solution can be kept at about 10° F. below room temperature, no further cooling would be required in most cases. No heating or cooling is usually required for the scrubber solution, although the scrubber can optionally be temperature controlled in the same manner.

Once an appropriate humidity is obtained within the enclosure, the enclosure can be filled with a suitable concentration of chlorine dioxide. This can be done by any of the previously described methods including bubbling air through a chlorine dioxide solution as in FIGS. 2 and 3, or by circulating the chlorine dioxide solution through the material transfer device and simultaneously recirculating the air from the enclosure through that device and back to the enclosure. While this is occurring, the humidity in the chamber can be controlled, as described above, by controlling the temperature of the circulating solution.

After the enclosure is filled with the desired concentration of chlorine dioxide and humidity, the enclosure is typically held at this condition for a suitable period to allow decontamination. Decontamination times can vary depending on the nature of the contaminating material and the severity of the contamination and can be determined by periodically testing the interior of the enclosure in pilot experiments or by testing during the decontamination process. During the decontamination the concentration of chlorine dioxide within the container and the humidity can be maintained as needed. Many methods for monitoring chlorine dioxide concentration are known and can be used.

To terminate the treatment, the air/chlorine dioxide gas can be vented to atmosphere, optionally through the material transfer device. When the material transfer device is used, chlorine dioxide solution can be removed from the device and replaced with a scrubber solution that is essentially free of chlorine dioxide. Air from the enclosure can then be drawn through the device and vented to atmosphere. As that occurs ambient air from the atmosphere can be used to replace the chlorine dioxide laden air in the enclosure until the concentration of chlorine dioxide in the enclosure drops to an acceptable level. Alternatively, the air can simply be recirculated through the material transfer device and into the enclosure until chlorine dioxide reaches an acceptable level.

Thus, the system illustrated in FIG. 4 can be used in a method in which the device used to contact the carrier gas with the aqueous solution is also used to remove the chlorine dioxide from the carrier gas.

In the embodiment of the invention illustrated in FIG. 4, a system comprising a packed column, a liquid pump, and a blower all configured with valves and fittings is connected to an enclosure to be decontaminated. Chlorine dioxide gas concentration and relative humidity in the enclosure can be measured using commercially available devices.

The inlet of the blower can be connected to the top of the material transfer device, and the outlet of the blower connected to the enclosure. The gas inlet of the material transfer device can also be connected to the enclosure. The connections to the enclosure are preferably located so that gas flows across the volume of the material transfer device with the flow path traversing as many compartments, side chambers, and conduits of the enclosure as possible to improve mixing in the enclosure. The enclosure is preferably sealed to prevent gas from escaping, and all light is preferably excluded from the enclosure.

A container containing hot water at about 140° F. can be connected to the drain of the material transfer device and the intake of the liquid pump can be submerged so that its end is near the bottom of the hot water. The liquid pump can be turned on and hot water circulated over the packing material in the material transfer device. The blower can then be turned on and gas and water circulated until the chamber reaches 65-80% relative humidity. One skilled in the art can easily determine how much water and what starting water temperature are required to fully humidify the enclosure, for example by monitoring humidity using a standard humidity sensor. Alternatively, supplemental heat or cooling can be provided to the material transfer device by methods described above. The relative humidity can be monitored to determine when to turn off the humidification segment of the process.

Alternatively a hot plate with an open pot containing an appropriate amount of water can be placed within the enclosure. The hot plate may be activated manually or automatically from the exterior of the enclosure or by means of a timer or a control system within the enclosure. Heating the water, along with a means of achieving an even distribution of the humidity, will achieve the same purpose of raising the humidity within the enclosure. At which point the hot plate can be turned off.

When the chamber has been humidified, the hot water can be removed from the material transfer device and discarded. A container of chlorine dioxide solution, as discussed above, can be used to replace the container of hot water. The solution circulates through the packing of the material transfer device where chlorine dioxide is stripped from the solution and passed into the carrier gas which is typically air. In one embodiment, a container of the chlorine dioxide solution can be provided that is large enough to supply the chlorine dioxide requirements for the entire cycle. For example, when the desired concentration of chlorine dioxide for treatment is 1500 parts per million by volume (1500 ppmv) and the chamber is 100 cubic feet in volume and the solution contains chlorine dioxide at 3000 parts per million by weight (ppmw), then it will take 100 cf*0.0015*0.175 lb/cf=0.026 lb of chlorine dioxide to fill the chamber once. Since a gallon of water weighs 8.3 lb, at 3000 ppmw, it contains 8.3*0.003=0.024 lb. Therefore, it will take a little more than about one gallon of solution to supply enough chlorine dioxide gas to fill the chamber once with a disinfectant level of treatment gas. If the chamber is well sealed, and made entirely of stainless steel or other material that does not react with or absorb chlorine dioxide, 2 gallons of solution could be provided to ensure that the concentration of the gas is more than sufficient to perform the decontamination. Larger quantities can be provided and would be needed in the event that the enclosure was not air tight.

The concentration of gas in the chamber can be monitored by methods known in the art, and the liquid pump for the material transfer device can be turned off when the enclosure reaches a suitable concentration. It can be turned back on when the concentration falls below suitable levels.

Alternatively, if the chlorine dioxide containing solution is used as a feed solution to the primary solution within the material transfer device the recirculating liquid pump may be left on continuously and feed solution may be metered into the primary solution as required.

When a treatment cycle is finished, the chlorine dioxide solution can be drained from the material transfer device, and replaced with a container of scrubber solution, which can be water or an aqueous solution containing a reducing compound such as sodium thiosulfate that will neutralize the chlorine dioxide. The pump and blower can be turned on and operated until the enclosure contains sufficiently low levels of chlorine dioxide. Spent scrubber solution can be drained from the system, sealed in a container, and safely disposed. When the system is used again, the hot water in the humidification cycle can be used to wash out any residual scrubber solution in the system, so it will not consume chlorine dioxide during the following treatment cycle. However, depending on the nature of the scrubber solution, a brief rinse cycle may be required before the system is stored or transported.

In some circumstances there can be partly used chlorine dioxide solution remaining in the container at the end of a treatment cycle. This can be used in the next decontamination cycle. In the event the solution became depleted of chlorine dioxide during the treatment cycle, the material transfer device could be briefly shut down and the spent solution could be replaced with a fresh solution.

One aspect of the disclosed method involves generating pure solutions of chlorine dioxide in distilled or deionized water or other suitable liquids. Typically, these ultra-pure solutions can be made at remote locations and shipped to the point of use, and at the point of use, the chlorine dioxide can be stripped from the solution and passed into flowing air. This approach differs from the prior art in that:

No significant levels of salts, dissolved chlorine, acids, or other impurities exist in the solutions. Thus, only pure chlorine dioxide, rather than acid vapors or chlorine gas is stripped from these solutions. This minimizes collateral damage to enclosures or its contents caused by impurities in prior art methods.

Moreover, the possibility of damage to enclosures or their contents caused by salt is removed in this process because no salt is dissolved in any droplets that form in the air stream that strips chlorine dioxide from the liquid. When chlorine dioxide is made off-site and stored before use, the solutions are not hot when used. This results in lower humidity levels which reduces condensation in enclosures.

It will be clear to one skilled in the art that the processes disclosed above could be readily automated so that a system could be pre-loaded with all of the necessary liquids and switching between the different liquids could be controlled by electromechanical mechanisms.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A process for handling chlorine dioxide comprising producing an aqueous chlorine dioxide solution at a remote location, wherein the aqueous chlorine dioxide solution contains less than 10% by weight, relative to the chlorine dioxide, of total impurities, shipping the aqueous chlorine dioxide solution to a point of use, releasing chlorine dioxide gas from the aqueous chlorine dioxide solution, and mixing the released chlorine dioxide gas with a carrier gas to produce a gas stream containing chlorine dioxide.

2. The process for handling chlorine dioxide of claim 1, wherein the carrier gas is air.

3. The process for handling chlorine dioxide of claim 1, wherein the chlorine dioxide gas is released from the aqueous chlorine dioxide solution by bubbling the carrier gas through the aqueous chlorine dioxide solution.

4. The process for handling chlorine dioxide of claim 1, wherein the chlorine dioxide gas is released from the aqueous chlorine dioxide solution by bubbling the carrier gas through the solution wherein the rate of $ClO_2$ gas production is controlled by the rate of carrier gas flow into the solution.

5. The process for handling chlorine dioxide of claim 1, wherein the chlorine dioxide gas is released from the aqueous chlorine dioxide solution under a vacuum.

6. The process for handling chlorine dioxide of claim 1, wherein the chlorine dioxide gas is released from the aqueous chlorine dioxide solution by heating the aqueous chlorine dioxide solution.

7. The process for handling chlorine dioxide of claim 1, further comprising introducing the chlorine dioxide gas into an enclosure.

8. The process for handling chlorine dioxide of claim 1, further comprising introducing the chlorine dioxide gas into an enclosure and disinfecting a portion of the contents of the enclosure.

9. The process for handling chlorine dioxide of claim 1, further comprising introducing the chlorine dioxide gas into an enclosure and disinfecting a portion of the contents of the enclosure and controlling the concentration of chlorine dioxide and relative humidity within the enclosure.

10. The process for handling chlorine dioxide of claim 1, further comprising controlling the relative humidity of the chlorine dioxide gas stream by raising or lowering the temperature of the aqueous chlorine dioxide solution that contacts the carrier gas stream.

11. The process for handling chlorine dioxide of claim 1, wherein a device used to contact the carrier gas with the aqueous solution is also used to control the humidity of the carrier gas.

12. The process for handling chlorine dioxide of claim 1, wherein a device used to contact the carrier gas with the aqueous solution is also used to remove the chlorine dioxide from the carrier gas.

13. The process for handling chlorine dioxide of claim 1, further comprising introducing the chlorine dioxide gas into a bio-safety cabinet and disinfecting a portion of the interior of the cabinet.

14. The process for handling chlorine dioxide of claim 1, further comprising introducing the chlorine dioxide gas into an enclosure selected from the group of enclosures consisting of a bio-safety cabinet, freezer, incubator and lyophilizer and disinfecting a portion of the interior of the enclosure.

15. The process for handling chlorine dioxide of claim 1, further comprising introducing the chlorine dioxide gas into a portion of a building and disinfecting a portion of the interior of the building.

16. A process for decontaminating an enclosure comprising:
   (a) producing an aqueous chlorine dioxide solution at a remote location, wherein the aqueous chlorine dioxide solution contains less than 10% by weight, relative to the chlorine dioxide, of total impurities,
   (b) shipping the aqueous chlorine dioxide solution to a point of use,
   (c) releasing chlorine dioxide gas from the aqueous chlorine dioxide solution and mixing the released chlorine dioxide gas with a carrier gas to produce a gas stream containing chlorine dioxide,
   (d) introducing the chlorine dioxide gas stream into the enclosure to obtain a disinfecting concentration of $ClO_2$ in the enclosure,
   (e) maintaining the relative humidity in the enclosure to between about 60 to 80%,
   (f) removing the $ClO_2$ after decontaminating the enclosure by circulating the gas through a scrubber containing a base and a reducing agent.

17. The process for decontaminating an enclosure according to claim 16, wherein the humidity in the enclosure is maintained by controlling the temperature of the $ClO_2$ solution.

18. The process for decontaminating an enclosure according to claim 16, wherein the reducing agent is sodium thiosulfate.

19. The process for decontaminating an enclosure according to claim 16, wherein the enclosure is selected from the group consisting of a bio-safety cabinet, freezer, incubator and lyophilizer.

20. A process for disinfecting comprising producing an aqueous chlorine dioxide solution at a remote location, wherein the aqueous chlorine dioxide solution contains less than 10% by weight, relative to chlorine dioxide, of total impurities, shipping the aqueous chlorine dioxide solution to a point of use, contacting the solution with a gas in an enclosure and releasing the chlorine dioxide from the solution into the enclosure such that a portion of the enclosure or contents in the enclosure is disinfected.

21. The process for disinfecting of claim 20, further comprising contacting the chlorine dioxide solution with the gas in the enclosure by spraying or atomizing the solution into the enclosure.

22. The process for disinfecting of claim 20, further comprising contacting the chlorine dioxide solution with the gas in the enclosure by conveying the solution into the enclosure.

* * * * *